United States Patent [19]

Kovacs

[11] Patent Number: 4,927,410

[45] Date of Patent: May 22, 1990

[54] METHOD FOR FABRICATING PROSTHESIS MATERIAL

[75] Inventor: Stephen G. Kovacs, Oldsmar, Fla.

[73] Assignee: University of South Florida, Tampa, Fla.

[21] Appl. No.: 273,298

[22] Filed: Nov. 18, 1988

[51] Int. Cl.$^5$ ............................ A61F 2/06; A61F 2/04
[52] U.S. Cl. ........................................ 600/36; 623/1; 623/66
[58] Field of Search ................... 623/1, 66; 600/36; 264/102, 310, 331.19; 528/68

[56] References Cited

U.S. PATENT DOCUMENTS

| | | | |
|---|---|---|---|
| 3,408,659 | 11/1968 | Thiele et al. | 623/1 |
| 3,425,418 | 2/1969 | Chvapil et al. | 623/1 X |
| 3,938,524 | 2/1976 | Sparks et al. | 600/36 X |
| 3,974,526 | 8/1976 | Dardik et al. | 600/36 X |
| 3,988,782 | 11/1976 | Dardik et al. | 600/36 X |
| 4,173,606 | 11/1979 | Stoy et al. | 623/66 X |
| 4,173,689 | 11/1979 | Lyman et al. | 521/64 |
| 4,286,341 | 9/1981 | Greer et al. | 623/1 |
| 4,323,525 | 4/1982 | Bornat | 623/1 X |
| 4,539,716 | 9/1985 | Bell | 600/36 X |
| 4,647,416 | 3/1987 | Seiler, Jr. et al. | 623/1 X |
| 4,729,766 | 3/1988 | Bergentz et al. | 623/1 |
| 4,787,900 | 11/1988 | Yannas | 623/1 |
| 4,816,339 | 3/1989 | Tu et al. | 623/66 |

FOREIGN PATENT DOCUMENTS

| | | | |
|---|---|---|---|
| 0143638 | 6/1985 | European Pat. Off. | 600/36 |

*Primary Examiner*—Alan Cannon
*Assistant Examiner*—N. Paul
*Attorney, Agent, or Firm*—Joseph C. Mason; Ronald E. Smith

[57] ABSTRACT

A method for fabricating human tissue prosthesis. The method produces a prosthesis that has mechanical compliance properties similar to that of body tissue. The prosthesis fabrication method utilizes, for example, a polyurethane urea-linked block copolymer system which in the cured state is a thermoset elastomer which has lumen surface qualities which are essentially optically flat. The formulation is essentially a single a single step process. A clean mandrel is horizontally clasped in the jaws of a variable speed motor and slowly rotated. The pre-polymer solution is placed on the rotating mandrel and thickness adjusted by a mechanical wiper. The rotating mandrel having pre-polymer of desired thickness is placed in a sub-atmospheric environment to remove dissolved gasses and permitted to initially cure while rotating. The final cure is achieved in a sub-atmospheric environment. Removal of the cured polymeric prosthesis from the mandrel is achieved by placing same in an aqueous solution at a temperature less than final cure temperature and then slipping the prosthesis from the mandrel. The combination of polymer system formulations and fabrication techniques has led to the development of vascular grafts which are non-thrombogenic, non-hemolytic, and which have a compliance factor closely matching its correspondent physiologic counterpart.

23 Claims, 4 Drawing Sheets

METHOD FOR FABRICATING PROSTHESIS MATERIAL

FIELD OF INVENTION

The present invention relates generally to artificial prosthesis material suitable for in vivo biocompatible implantation. It particularly relates to a method of fabricating human tissue prosthesis utilizing a polyurethane urea-linked block copolymer system which in the cured state is properly considered as a cast thermoset elastomer.

DESCRIPTION OF THE RELATED ART

In recent years, study on artificial prosthesis has proceeded with some progress in vascular surgery. Typical of these prior art materials include woven Dacron (USCL, Co. Ltd. of U.S.A.) and the Gore-Tex prosthesis (Gore Co. Ltd. of U.S.A.). Although clinically used, these materials have serious disadvantages. Poor patency is a recurring problem, particularly with vessels having 6 mm or less diameter.

BACKGROUND

The utility of synthetic polymers as replacement material for various types of human tissue has been substantially advanced by recent developments in improved compatibility characteristics of polymer compositions with the numerous chemical environments of the body. Although improvements in body tissue and blood compatibility (hereinafter referred to as "compatibility") have enabled more extensive use of synthetic polymers in prosthetic surgery, the continued failure of many of these implants has greatly impeded progress in treatment of persons requiring replacement of human tissue.

It has now been discovered that many of these failures were the product of mechanical mis-match, as well as compatibility rejection. Inasmuch as the effects of these two causes are quite similar—clotting of the blood and tissue rejection—the subsequent failure of the newer nonthrombogenic materials was viewed as simply a further rejection due to other chemically adverse reactions to the prosthetic implant.

Recent investigation of vascular grafts has disclosed, however, that such thrombosis and accompanying graft failure of these nonthrombogenic materials was the result of mechanical mis-match between the graft and natural tissues. Such mis-match includes a variance in elastic response and other physical properties such that the grafted material does not mechanically respond in consonance with the natural tissue. The resulting traumatization and other adverse tissue reactions cause clotting and occlusion of the vein, similar to that experienced with chemical noncompatibility.

These effects of compliance mis-match are particularly troublesome in small diameter vascular grafts. The continual variations of blood pressure cause a recurring pulsing motion resulting in constant expansion and contraction of the vascular tissues. Where the grafted material is not of an equivalent compliance with the natural vascular tissue, the inconsonant response of the grafted portion results in fluid turbulence and direct tissue damage at the sutured juncture. If the diameter of the fluid path is large or if the rate of fluid flow is high, the adverse effects of thrombosis may not be severe. This is true, for example, in the larger vessels such as the aorta which has both large diameters and substantial blood flow. If, however, these favorable conditions are not present, blood clots accumulate and frequently result in occlusion of the fluid path. For this reason, none of the previous grafts (polymer, Goretex, Dacron, or ceramic) have been effective in the venous side of the circulatory system or where the vessel diameter has been less than 6 mm on the arterial side. The combination of minimal diameter and/or reduced blood flow have precluded the effective use of synthetic material for such vascular grafts.

Because of the unavailability of suitable synthetic materials with the required compliance characteristics, vascular grafts for small diameter blood vessels and coronary bypass requirements now require the transplantation of saphenous vein from the leg of the patient or other vein material from the less critical parts of the circulatory system. The procedure is limited, however, due to potential risks of resultant circulation failure, particularly in older persons. Furthermore, it is not uncommon for an older patient to have failing saphenous veins, requiring the use of potential donors with the accompanying risks of antigenic reactions. The seriousness of these limitations is illustrated by the fact that approximately 60% of the amputations currently performed in hospitals are the result of vascular failure. A final, if perhaps sobering aspect of saphenous vein harvesting for coronary bypass is the fact that they are only available for use once.

Similarly, rejection of prosthetic materials in other body systems has been commonly experienced. Frequently, the treatment of such areas as the common bile duct, urethra, ureta and hydrocephalic tubes includes the need of tissue replacement which has previously been unsuccessful due to the concurrent needs of compatibility and mechanical compliance. Such requirements are not satisfied by synthetic materials now available in the commercial market.

Earlier polyurethane block copolymers, such as Biomer TM and Cardiothane TM, are mostly in the family of thermoplastic elastomers, which are basically characterized as softening or yielding to deformation due to temperature or plastic-flow inducing stresses. Most thermoplastic polyurethane elastomers have a specific formulation or component mix ratio which produces an elastomer with essentially one set of material characteristics, i.e., no variation of characteristics compatibility. Prior vascular graft fabrication techniques (Lyman - U.S. Pat. No. 4,173,689, Kira - U.S. Pat. No. 4,725,273) sought to develop graft compliance factors required for physiologic use by means of various material elasticity producing techniques, such as controlling the dispersion of inter-wall voids or bubbles, or the formation of graft walls having both through and inter-wall pore-/hole dispersion.

Clinical evidence shows that polyurethane elastomer porous structure grafts experience repeated failures due to thrombosis and inflammation (Ref. "POLYURETHANES IN MEDICINE, Cooper, CRC Press - 1986).

It should be noted that there is a substantial difference in elongation response between the compared materials. This variance becomes even more acute in the body environment where the forces to which mechanical response is required are often small. Consequently, synthetic polymers which appear to be sufficiently elastic when being manually stretched, will give little responses to very slight pressures which occur in the body. Unless the prosthesis material has mechanical properties matching such tissue to which it is to be connected, there will be an adverse reaction tending toward rejection of the material.

OBJECTIVES OF THE INVENTION

It is therefore an object of the present invention to provide a synthetic material having mechanical compliance with body tissue.

It is a further object of the present invention to provide a mechanically compliant synthetic material having blood and body tissue compatibility characteristics suitable for prosthesis use.

It is still a further object of this invention to provide a mechanically compliant synthetic material having blood and body compatibility characteristics suitable for prosthesis use, being adaptable for use as surgical graft, replacement material or covering for numerous types of organic tissue.

It is another objective of this invention to provide such a prosthesis material having suitable characteristics to facilitate suturing or methods of attachment to the subject area of treatment.

It is still another object of the present invention to provide a usable method for fabrication of the aforementioned materials, such method being to produce a copolymer product having a variety of mechanical compliance characteristics suitable for various types of tissue prosthesis.

SUMMARY OF THE INVENTION

The present invention achieves these and other objectives by providing a method of fabricating a non-thrombogenic, non-hemolytic thermoset elastomer vascular prosthesis. By single step mixing process at room temperature and atmospheric pressure, the elasticity is selected to provide a prosthesis with compliance values ranging from 0.1 to 0.8. The mix-ratios of components enable elastomer grafts to be wiper-formed on a rotating mandrel with the cured grafts having wall thickness functionally related to bore diameter, and having a range of SHORE hardness values from 50A to 90A.

A method of the present invention produces a prosthesis that has mechanical or physical compliance properties similar to that of body tissue. The prosthesis fabrication method utilizes, for example, a polyurethane urea-linked block copolymer system which in the cured state is a thermoset elastomer which has lumen surface qualities which are essentially optically flat. The formulation is essentially a single step process. A clean mandrel is horizontally clasped in the jaws of a variable speed motor and slowly rotated. The pre-polymer solution is placed on the rotating mandrel and thickness adjusted by a mechanical wiper. The rotating mandrel having pre-polymer of desired thickness is placed in a sub-atmospheric environment to remove dissolved gasses and permitted to initially cure while rotating. The final cure is achieved in a sub-atmospheric environment. Removal of the cured polymeric prosthesis from the mandrel is achieved by placing same in an aqueous solution at a temperature less than the final cure temperature and then slipping the prosthesis from the mandrel. The combination of polymer system formulations and fabrication techniques has led to the development of vascular grafts which are nonthrombogenic, non-hemolytic, and which have a compliance factor closely matching its correspondent physiologic counterpart.

In one embodiment of this invention there is provided a method of fabricating prosthesis material for use with a living body which comprises:

(a) preparing a polymerizable thermosetting material by mixing components thereof at about ambient temperature and about atmospheric pressure;

(b) introducing the thermosetting material to the surface of tubular forming means having rotatability about a substantially horizontal axis thereby forming a relatively thin film of thermosetting material thereon;

(c) subjecting the thin film to sub-atmospheric pressure at about ambient temperature thereby imparting isotropic characteristics to the film;

(d) contacting the thin film with wiper means in order to remove excess material from the film thereby achieving desired film thickness; and (e) curing the thin film to a stable physical structure of prosthesis material.

A further embodiment of the method invention utilizes a polymerizable thermosetting material selected from the class of material known as oligomeric diaminobenzoates.

A still further embodiment of the method of the invention utilizes oligomeric diaminobenzoate which has been chain extended by modified diphenylmethane diisocyanate or by methylene bis-p-phenyl-isocyanate.

Another embodiment of the method of the invention produces a prosthesis material whose surface is optically flat and has a compliance value ranging from 0.1 to 0.8.

Still another embodiment of the invention is a blood and tissue compatible artificial prosthesis material prepared in accordance with the methods of this invention wherein the prosthesis material has physical properties of compliance approximating those of organic tissue counterpart.

A still further and another embodiment of the invention is a method for replacing soft body tissue comprising (a) preparing prosthesis material in accordance with the methods of the invention and (b) applying the prosthesis material to a portion of a living body to form an integral combination of prosthesis material and living tissue.

A more specific embodiment of the invention is a method of fabricating an artificial prosthesis material for use with a living body which comprises:

(a) preparing a liquid polymer solution having thermosetting properties and physical properties of compliance and elasticity substantially the same as that of soft body tissue, by mixing desired components at about atmospheric pressure and about ambient temperature;

(b) depositing an excess of the polymer solution to the surface of a substantially horizontal rotating mandrel located in housing means;

(c) subjecting the interior of the housing means to sub-atmospheric pressure sufficient to degas the deposited polymer solution;

(d) contacting the deposited polymer solution on the rotating mandrel with wiper means thereby adjusting the thickness of the polymer solution on the rotating mandrel to desired thickness;

(e) curing the polymer solution on the rotating mandrel in the housing means for a first predetermined time and at about ambient temperature and about atmospheric pressure sufficient to initially cure the polymer to a tacky state;

(f) removing the mandrel having deposited thereon the initially cured polymer from the housing means;

(g) subjecting the initially cured polymer to temperature and pressure conditions and at second predetermined time sufficient to finally cure the polymer to a stable physical structure of prosthesis material;

(h) immersing the mandrel having deposited thereon the stable physical structure of prosthesis material in an aqueous solution under conditions sufficient to cause a thin film of aqueous solution to be deposited between the outer surface of the mandrel and the inner surface of the cured polymer; and (i) removing the prosthesis material from the mandrel.

A still more specific embodiment of the more specific embodiment of the method of this invention comprises a first predetermined time that is less than the second predetermined time and the conditions sufficient to deposit a thin film of aqueous solution including a temperature less than the temperature sufficient to finally cure the polymer.

A specific product embodiment comprises a blood and tissue compatible artificial prosthesis material prepared in accordance with a method of the present invention.

BRIEF DESCRIPTION OF THE DRAWINGS

FIG. 4 is a representative view of a wiper or doctor blade useful in the practice of the present invention.

FIG. 5 is a representative view of a mandrel having deposited thereon a prosthesis material of the present invention.

FIG. 6 is a photomicrograph of the surface of the inventive prosthesis magnified at 2000x.

DESCRIPTION OF THE PREFERRED EMBODIMENT GENERAL AND BEST MODE

Figure 1:
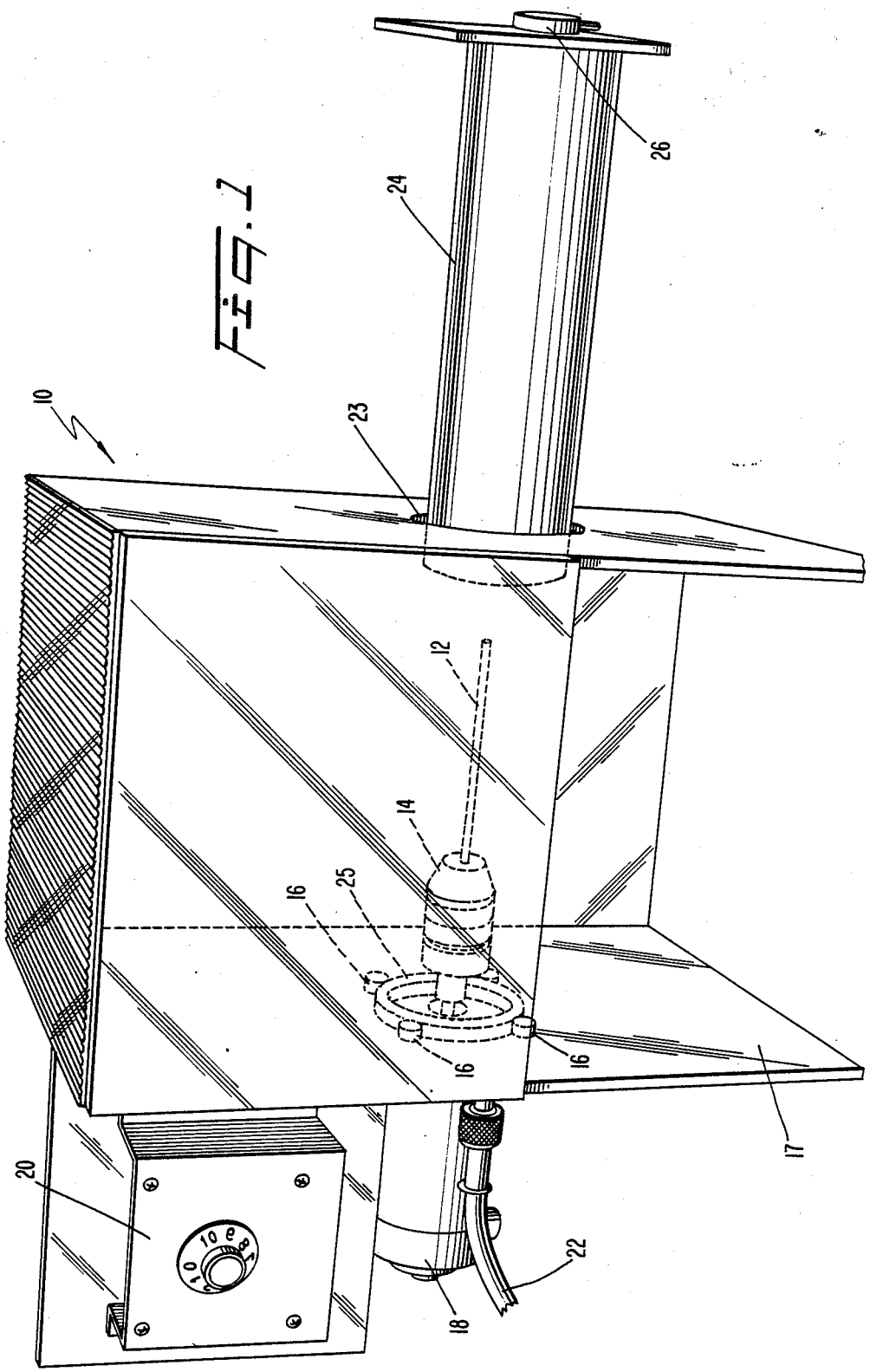
FIG. 1 is a prospective view of an apparatus for producing the prosthesis of the present invention.

The artificial prosthesis is fabricated utilizing a segmented co-polyurethane and more preferably a hydrophilic polyurethane.

Formulation of the polyurethane co-polymer material is essentially a single step process wherein the entire desired prosthesis characteristics are obtained by mixing in a single operation the desired components. For example, the following mixture has been found advantageous in the practice of this invention: (1) oligomeric diaminobenzoate as a pre-polymer, (2) modified diphenylmethane diisocyanate chain extender, and (3) appropriate reaction and material characteristic modifiers; all at about room temperature and about atmospheric pressure. Preferably, no solvent is used.

Since it is well established that both arterial and vascular compliance is principally controlled by bore diameter and wall thickness, the method of the invention enables the fabrication of a vascular prosthesis wherein the desired compliance is achieved by means of an elasticity formula factor in the elastomer composition which is consequently determined by wall thickness requirements.

The artificial prosthesis fabricated by a method of the present invention has been found to have the following characteristics: (1) the lumen surface is optically clear at 2000X with no surface irregularities or anomalies such as bumps, pits, voids; however, waviness of the order of 0.25 u may be observed; (2) totally non-thrombogenic and non-hemolytic as evidenced by in vivo testing; (3) non-toxic, non-inflammatory tissue reactions; (4) uniform structural characteristics, i.e., it is isotropic with uniform tensile strength and elasticity in both longitudinal and radial directions; (5) enables resilient closure around penetrating sutures; (6) steam autoclavable; and (7) is capable of compliance formulation nearly matching the requirements defined by graft bore diameter and wall thickness of the living vessel counterpart.

The polyurethane block copolymer used for the vascular graft fabrications is of a class identified as oligomeric diaminobenzoates. Oligomeric diaminobenzoates are usable in polyurethane cast elastomers because their reactivity is different from that of other MDI-amine formulations commonly used in reaction injection molding applications.

Conventional approaches to the preparation of cast elastomers involve the reaction of a short-chain diamine with a long-chain polymer terminated with toluene diisocyanate. Another commonly used system involves reacting diols with resins capped with MDI, or methylene diisocyanate or methylene-bis-p-phenyl-isocyanate.

The use of either system usually is dictated by the required physical properties of the application.

Oligomeric diaminobenzoates reverse the typical arrangement of the reacting species and have the amine functionality capped onto the ends of the soft segment.

Chain extension is accomplished by using MDI, modified forms of monomeric MDI or MDI-containing resins as the hard segment.

Elastomers prepared from these formulations exhibit the best overall physical properties of cast, thermoset elastomers, although other soft segments can be used—polyester, polycarbonate, or polypropylene glycol.

TDI-amine elastomers contain urethane and urea linkages, while MDI-polyol elastomers contain only urethane linkages. MDI-polyamine elastomers contain only urea linkages. Preliminary investigations by dynamic mechanical analysis indicate oligomeric diaminobenzoate-MDI elastomers have a higher service temperature than conventional elastomers, which might be the result of the absence of the urethane linkage.

Specifically, and preferred elastomers for the practice of this invention include VIVATHANE ™, the generic components of which comprise the series of polyurethane copolymer obtained by formula ratio variations of the presently used chemical components; these components are generically described as:

1. Base component: (soft chain component) (referred to as VIVATHANE ™) Oligomeric diaminobenzoates
   Note: Other soft chain components, e.g., polyether, polycarbonate, and polypropylene glycol can also be used for the molecular structure "back bone."
2. Chain extenders: (used to control quality of flexibility or hardness)
   a. Diphenylmethane Diisocyanate
   b. Modified 4,4'-Diphenylmethane-Diisocyanate
3. Reaction and characteristics modifiers:
   a. Methyl ethyl ketone (MEK)
   b. Ethyl alcohol c. Polyester
d. Polyether

BASIC FABRICATION

Fabrication of a vascular prosthesis in accordance with this invention comprises the following basic procedure:

(1) A clear fire-polished, amorphous structure mandrel, e.g., a quartz rod, having the required diameter for the prosthesis desired, is centered in a chuck.

(2) The chuck spindle is driven by a variable speed motor (0–100 rpm).

(3) The chuck and mandrel project into a dust-free chamber or housing maintained at a slight + atmospheric pressure, so as to prevent micro- and mini-airborne contaminants such as dust, hair, lint, etc. from entering.

(4) The several components of the liquid polymer/elastomer are single step mixed, i.e., simultaneously in accordance with a range of mix ratios associated with the graft bore diameter and component physiologic wall compliance factor.

(5) Component mix ratios vary from (a) diaminobenzoate pre-polymer to modified diphenylmethane diisocyanate (MDI chain extender) 3:1–6:1

(b) linkage modifier: 5%–35% by volume, wherein the linkage modifier is of the diisobutyl adipate class.

6. Upon completion of component mixing, an adequate thick film, approximately 1.5 mm thick, is laid or spread onto the rotating glass or quartz mandrel for the graft length desired plus 10% for trim.

7. Mandrel rotation is determined according to graft diameter and length, since both centrifugal force and liquid elastomer surface tension forces are used in developing initial film thickness prior to degassing. Rotation speed would be readily determined by one skilled in mandrel casting.

8. Upon obtaining a reasonably uniform thick walled casting, a cylindrical sleeve is positioned within the chuck mandrel chamber so as to create a sealed inner cylindrical chamber of smaller volume than the main chamber. The cylindrical chamber is introduced through an access port on the wall opposite the chuck mandrel wall. It is centrally positioned against a circular sealing gasket centered around the chuck position, by means of the extended centering pins located on a circle equal to the outside diameter of the sealing tube chamber. This usually is all done in less than 15 seconds.

9. Once the inner chamber is positioned against the isolation seal gasket, a vacuum is produced within the isolation cylinder by means of the vacuum exhaust line which terminates within the sealed isolation volume.

10. The vacuum is allowed to exhaust the sealed inner chamber so as to cause degassing of entrapped air from the rotating elastomer film, thus providing the film with isotopic properties.

11. During degassing—at an appropriate time as determined by the degassing condition of the rotating liquid elastomer film—the vacuum is momentarily popped (or interrupted) by quickly allowing air at atmospheric pressure to enter from an access port at the end of the cylinder opposite from the sealing end; by means of a solenoid fast-acting valve, or any other rapid opening and closure means.

12. This sudden inrush of air serves to further assist in degassing by virtue of the sharp transient pressure rise causing a sudden implosion of air bubbles contained in the elastomer film.

13. This alternate vacuum pumping and sudden air implosion degassing is a procedure whose repetition, if any, is determined by bore diameter and film thickness.

14. When degassing is complete (determined by visual inspection against projected background lighting), the vacuum is shut off, the inner isolation chamber is removed.

15. At this point, the final desired graft wall thickness is obtained by means of a specially designed calibrated film wiping tool.*

*Note: The wiping tools can be made up in advance and are reusable.

16. The wiping tool or doctor blade consists of a length of flame polished, uniform diameter quartz rod having a length greater than the graft length. At each end of the wiping rod, 1-mil thick stainless steel tape, ½" wide, is wound on in layers required to give the final wall thickness of the graft being fabricated, i.e., if a 0.020" wall thickness is desired, then 20 turns are wound on each end, both starting and stopping at identical positions.

17. The space between the enlarged diameter wall thickness tape rings is equal to the required graft length plus 10% trim.

18. The diameter of the wiping tool is, from experience, about two times the graft diameter although other diameters may be used. Having a wiping tool that is twice the diameter of the mandrel permits a maximum removal of excess film thickness during the first wipe.

19. The calibrated wall-thickness forming or wiping tool is placed in a position parallel to the liquid elastomer coated rotating mandrel.

20. It is brought into mechanical parallel contact with the rotating elastomer coated mandrel at the surfaces defined by the positions of the ½" wide tape rings or flanges.

21. When in parallel flange contact, approximately 90–95% of excess liquid elastomer is wiped off of the rotating mandrel, leaving a liquid elastomer film on the rotating mandrel having a fairly uniform wall thickness of the desired value.

22. The excess liquid elastomer removed by the wiping tool on the first wipe is removed by, for example, lint-free stripping pads.

23. The wiping tool is again placed in parallel mechanical contact with the rotating film covered mandrel in order to remove the slight amount of excess film left on the mandrel due to surface tension forces existing at time of first wiping tool withdrawal. These surface tension forces cause some of the excess first wiped film to withdraw or be pulled back onto the rotating mandrel on first wiping tool retraction.

24. Completion of the second wiping tool removal will result in a liquid elastomer film having acceptable uniform thickness.

25. At this point, the elastomer has become sufficiently stable to retain dimensional uniformity, due to curing initiative. Time to this point is approximately 5 to 25, typically, 10–12 minutes.

26. Next, the mandrel is reduced in rotational velocity by about one-half of the velocity used in film forming. This rotation velocity is maintained for approximately one hour, during which time the elastomer has self-cured, at room temperature, to essentially a tack-free state; sometimes referred to as the "spindle cure."

27. After the self-curing procedure, the elastomer coated mandrel is placed for final cure in a 40° to 75°, preferably about, 50° C. oven for about 2–10 hours, preferably, five hours; sometimes referred to as the "oven cure."

28. Because the specific formulations used in the vascular prosthesis fabrication produce an essentially non-hydrolytic thermoset polyurethane copolymer, (water absorption less than about 0.3% by weight), this non-hydrolytic property is used to enable removal of the cured vascular prosthesis from the mandrel.

29. The combined cured elastomer prosthesis and mandrel are fully immersed in a container of aqueous solution such as de-ionized water maintained at a temperature less than the curing temperature, such as about 45° C., if, for example, the oven cure was 50° C., for a period of from 1-6, preferably, about three hours; although longer times up to 2-3 days may be used; sometimes referred to as the "hydrate cycle."

30. During this time, a water film approximating several molecular thicknesses, forms between the inside surface of the cured prosthesis and the surface of the mandrel, by means of capillary intrusion of the water film into the prosthesis/mandrel interspace.

31. Upon complete interspace filling, the water film provides a good lubricity condition which enables the elastomer vascular prosthesis can be gently slipped off the mandrel.

32. However, for purposes of ease of handling and autoclaving, the elastomer prosthesis is left on the glass mandrel after ready removal state is effected.

33. The elastomer prosthesis on the mandrel is preferably placed in a Pyrex screw cap tube of suitable dimensions and then autoclaved on a standard liquid cycle.

Referring now to the drawings in greater detail, FIG. 1 shows an apparatus useful in the practice of the present invention. Housing 10 encloses mandrel 12 fixedly attached to rotatable means 18, e.g., variable drive electric motor together with rotating speed control means 20, by means of adjustable chuck means 14. Associated with housing means 10 is movable secondary enclosure means 24 which may be a cylindrical tube or other hollow sleeve-like device having entry means into housing 10 by way of access hole 23. Enclosure means 24 has quick release valve 26 at its distal end. The proximal end of enclosure means 24 when inserted into housing 10 fits against seal means 15 and rests between guide pins 16 for ease of accurate insertion against seal means 15, e.g., an O-ring. When fully inserted, enclosure means 24 may be evacuated to sub-atmospheric pressure by means of a vacuum pump (not shown) which expels the atmosphere of means 24 through connection device 22.

Housing 10 may be open on the lower front 17 for access to mandrel 12 or it may have open and closure means (not shown) or may have other features readily recognizable by the art for access to mandrel 12 during the practice of the present invention.

In one mode for practice of the invention, as aforesaid, and now referring to FIG. 1, liquid prosthesis material is deposited on the mandrel 12 which is held by chuck 14 and rotated by electric motor 18. Speed of rotation is controlled by rheostat means 20, which is capable of controlling rotational speed between 0-100 rpm. Use of a spatula such as shown in FIG. 6 is useful for this purpose.

Figure 2:
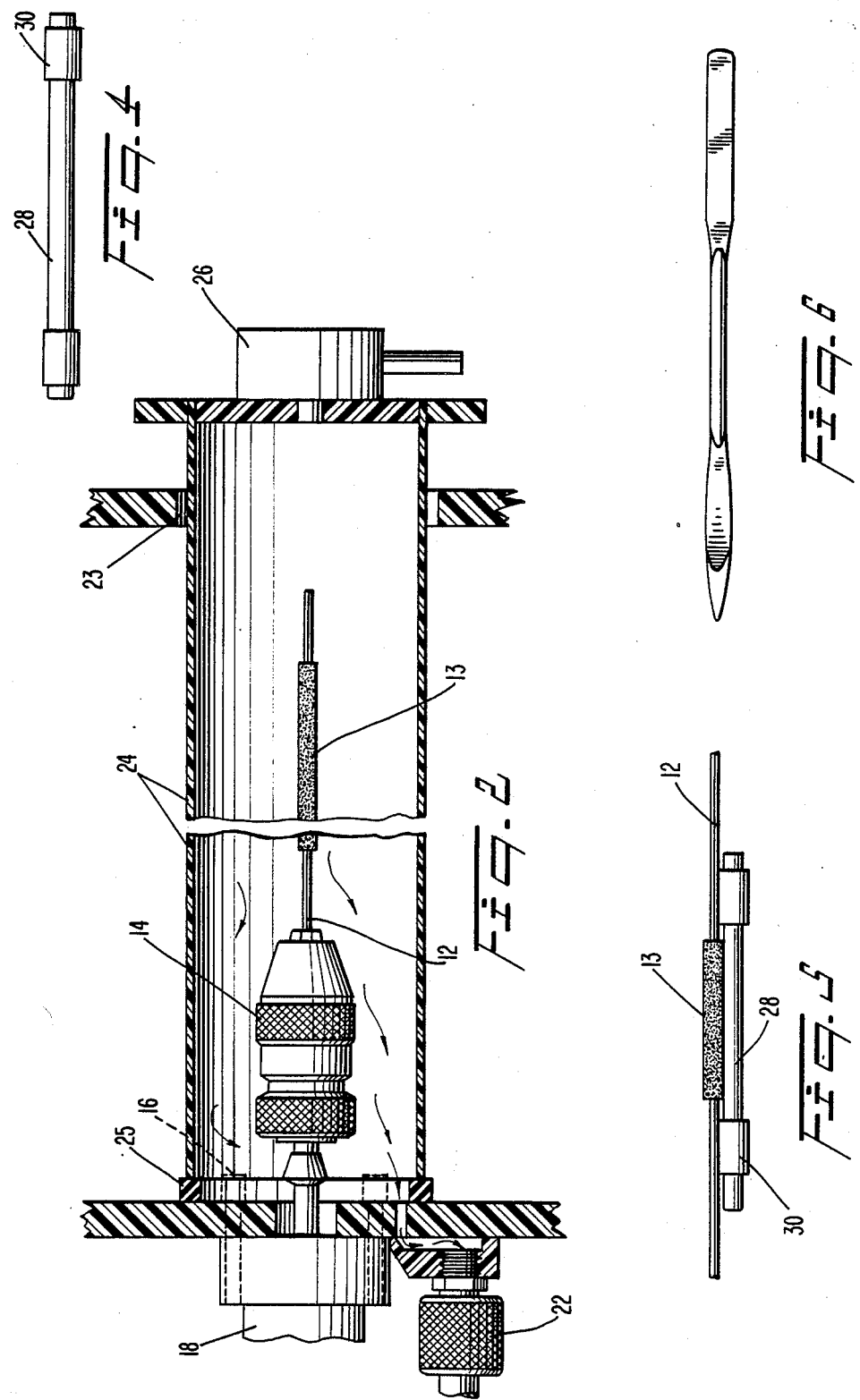
FIG. 2 is a further prospective view of the relation between the housing of the apparatus and the vacuum chamber.
Figure 3:
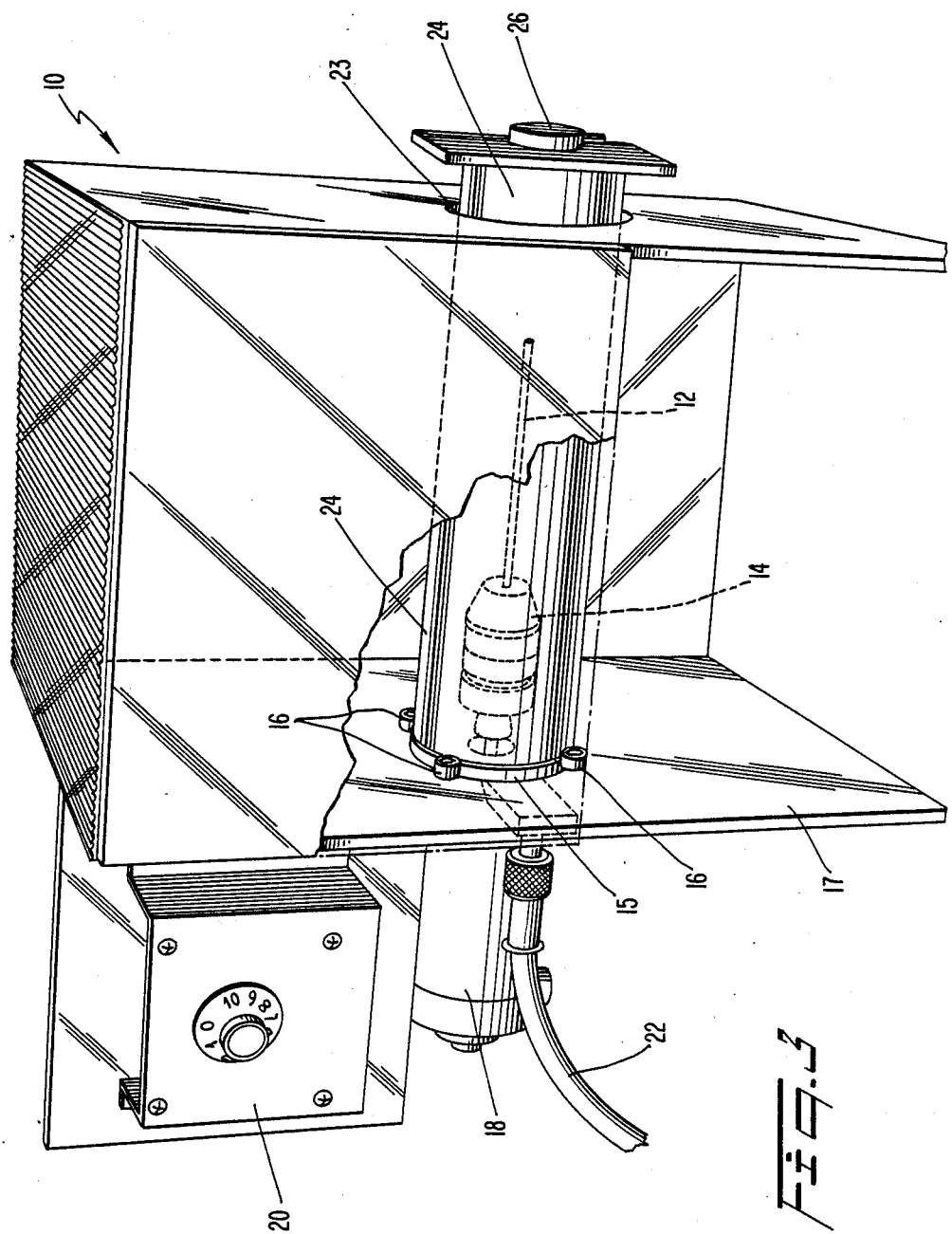
FIG. 3 is a prospective cut-away view of an apparatus for producing the prosthesis of the present invention showing the secondary enclosure means in place.

As illustrated in FIGS. 2 and 3, while continuing the rotation of mandrel 12 containing the deposited film of prosthesis material 13, enclosure means 24 is moved into position through access opening 23 until its proximal end is fixed and aligned with guide or retaining pins 16 firmly against seal ring 25. Release valve 26 is closed. A vacuum is drawn inside tube 24 by a vacuum pump (not shown) through vacuum hose connection device 22. After degassing of the material film 13, rapid release valve means 26 is opened to implosively return enclosure means 24 to atmospheric pressure. Enclosure means 24 is withdrawn from housing 10 through opening 23 (see FIG. 1).

Referring to FIG. 4, wiper or doctor blade 28 is prepared by wrapping thin layers of material 30, such as foil, on each end of blade 28. This wiping tool 28 is then placed in contact with rotating mandrel 12, as illustrated in FIG. 5. Wiper 28 contacts film 13 on mandrel 12 and wrapped ends 30 contact mandrel 12 at locations without a deposit of film. In this spaced relationship, excess material is removed from the rotating mandrel 12 thereby preparing a film of deposited material 13 of desired thickness on mandrel 12. Wiper 28 is removed from contact with mandrel 12.

Rotational speed is reduced by approximately one-half and the film left to self-cure, at room temperature, for approximately one hour.

Subsequent to self-curing, the mandrel 12 with film 13 is removed from housing 10 and oven cured at a temperature of about 50° C. for approximately 5 hours.

Figure 8:
Figure 7:
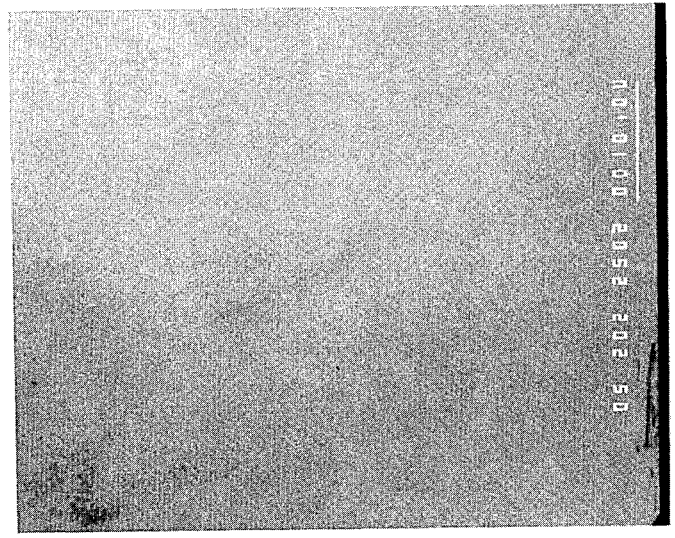
FIG. 7 is a photomicrograph of the surface of a prior art prosthesis material magnified at 200x.

The cured prosthesis on the mandrel is then immersed in de-ionized water at about 45° C. for about three hours. Water film forms between the prosthesis and mandrel thereby providing sufficient lubricity to permit the formed prosthesis to be slipped off the mandrel. The inside diameter surface of the prosthesis of this invention is optically flat as evidenced by the photomicrograph magnified 2000x shown in FIG. 7. The prosthesis material of the prior art (Goretex) magnified to 200x as in FIG. 8 shows considerable unevenness, thus having serious blood clotting protuberances.

The resultant product of the rotating mandrel cast elastomer film process is blood and body-tissue compatible thermoset copolymer whose mechanical compliance may be adjusted to match various tissues within the body. These synthetic materials have been produced which mechanically respond in essentially the same manner as body vascular tissue. The harmonious operation of such grafts has been evidenced by the natural pulsing motion of the graft in the actual circulation system of test animals. Such grafts have been successfully implanted in dogs whose rate of thrombosis is much higher than that of human systems.

Potential uses of the cast film polymer are foreseeably extensive. In addition to significant application in vascular graft treatment, the material may be utilized for prosthesis treatment of stomach and bladder tissue, as well as for prosthetic nerve cuff material. The placement of small diameter duct work of the body is another major medical application having specific utility in urethra, ureta, common bile duct and similar prostheses. The cast film polymer of this invention may be formed in sheets and applied as a skin covering in burn treatment or for other skin covering applications. Additional uses may develop where the prosthesis requirements include the requirements of compatibility and mechanical compliance. This method permits fabrication of numerous shapes and forms by varying the surface configuration of the forming device used in the film or form casting process.

EXAMPLES

The following summarizes the results obtained from the practice of the inventive method:

No. 1

Liquid thermosetting prosthesis starting material was prepared by mixing in a glass container 3.5 ml of VIVATHANE TM, 3.0 ml of diisobutyl adipate and 1.0 ml of methylethylketone (MEK) at room temperature (24° C.) and atmospheric pressure. This material was placed on the rotating mandrel and processed in accordance with the methods described for this invention. After a spindle cure of two hours at 24° C. with a mandrel rotational speed of 20 rpms; an oven cure of two hours at 50° C.; and, an overnight hydrate cycle at 45° C. in water, the finished prosthesis material was easily removed from the mandrel, had a wall thickness of 0.004" and an internal diameter of 3 mm; its color was good, transparency good, and its internal surface was smooth as typically shown in FIG. 7. Two wipes of the wiping tool were used to obtain wall thickness.

No. 2

Liquid starting material was prepared and processed as generally described in Example No. 1 under the following conditions:

| A. | VIVATHANE TM | 3.5 ml | Pre-starting |
| | Diisobutyladipate | 3.0 ml | prosthesis material |
| | Dibutylamine | 0.5 ml | |
| | MEK | 0.5 ml | |
| B. | Spindle Cure: | 2 hours @ 24° C. and 20 rpms | |
| | Oven Cure: | Overnight @ 50° C. | |
| | Hydrate Cycle: | 2 hours at 45° C. in water | |
| C. | Results | Wall thickness: 0.004" (one wipe) | |
| | | Internal diameter: 3 mm | |
| | | Color: good | |
| | | Transparency: good | |
| | | Surface: smooth | |

No. 3

The procedure of Example No. 1 was repeated under the following conditions:

| A. | VIVATHANE TM | 3.5 ml | Pre-starting |
| | Diisobutyladipate | 3.0 ml | prosthesis material |
| | Dibutylamine | 0.5 ml | |
| | MEK | 0.35 ml | |
| B. | Spindle Cure: | 1.5 hours @ 24° C. and 30 rpms | |
| | Oven Cure: | 2 hours @ 50° C. | |
| | Hydrate Cycle: | 2 hours @ 45° C. in water | |
| C. | Results | Wall thickness: 0.0025" (one wipe) | |
| | | Internal diameter: 3 mm | |
| | | Color: good | |
| | | Surface: smooth | |

Note: The prosthesis had a tendency to wrinkle easily.

No. 4

The procedure of Example No. 3 was repeated with the same pre-starting material composition under the following conditions:

| A. | Same as Example No. 3. | |
| B. | Spindle Cure: | 2 hours @ 24° C. and 40 rpms |
| | Oven Cure: | 2 days @ 50° C. |
| | Hydrate Cycle: | 2 hours @ 45° C. in water |
| C. | Results | Wall thickness: 0.0020" (3 wipes) |
| | | Internal diameter: 3 mm |
| | | Color: good |
| | | Surface: smooth |

Note: The prosthesis had a tendency to wrinkle easily and was removed from the mandrel with some difficulty.

No. 5

The procedure of Example 1 was repeated under the following conditions:

| A. | VIVATHANE TM | 3.5 ml | Pre-starting |
| | Diisobutyladipate | 3.0 ml | prosthesis material |
| | Dibutylamine | 0.35 ml | |
| | MEK | 0.35 ml | |
| B. | Spindle Cure: | 2 hours @ 24° C. @ 30 rpms | |
| | Oven Cure: | 2 days @ 50° C. | |
| | Hydrate Cycle: | overnight @ 45° C. in water | |
| C. | Results | Wall thickness: 0.002" (one wipe) | |
| | | Internal diameter: 3 mm | |
| | | Color: good | |
| | | Surface: smooth | |

Note: The prosthesis had a tendency to wrinkle.

No. 6

The procedure of Example 1 was repeated under the following conditions:

| A. | VIVATHANE TM | 3.5 | Pre-starting |
| | Diisobutyladipate | 3.0 ml | prosthesis material |
| | MEK | 0.35 ml | |
| B. | Spindle Cure: | 1.5 hours @ 24° C. @ 50 rpms | |
| | Oven Cure: | 2 hours @ 50° C. | |
| | Hydrate Cycle: | 2 hours @ 45° C. in water | |
| C. | Results: | Wall thickness: (0.018") | |
| | | Internal diameter: 3 mm | |
| | | Color: good | |
| | | Transparency: good | |
| | | Surface: smooth | |

No. 7

The procedure of Example 3 was repeated with the same pre-starting material composition under the following conditions:

| A. | Same as Example No. 3 | |
| B. | Spindle Cure: | 2 hours @ 25° C. @ 10 rpms |
| | Oven Cure: | 2 hours @ 50° C. |
| | Hydrate Cycle: | 2 hours @ 45° C. in water |
| C. | Results | Wall thickness: 0.006" |
| | | Internal diameter: 4 mm |
| | | Color: good |
| | | Transparency: good |
| | | Surface: smooth |

No. 8

The procedure of Example 5 was repeated with the same starting material composition under the following conditions:

| A. | Same as Example No. 5 | |
| B. | Spindle Cure: | 2 hours @ 25° C. @ 40 rpms |
| | Oven Cure: | 2 hours @ 50° C. |
| | Hydrate Cycle: | overnight @ 45° C. in water |
| C. | Results | Wall thickness: (0.012") |
| | | Internal diameter: 3 mm |
| | | Color: good |

-continued

| | |
|---|---|
| Transparency: good | |
| Surface: smooth | |

No. 9

The procedure of Example 1 was repeated under the following conditions:

| A. | VIVATHANE ™ | 3.0 ml | Pre-starting |
| --- | --- | --- | --- |
| | Diisobutyladipate | 2.0 ml | prosthesis material |
| | Dibutylamine | 1.4 ml | |
| | MEK | 1.0 ml | |
| B. | Spindle Cure: | 1.5 hours @ 24° C. @ 25 rpms | |
| | Oven Cure: | 4 hours @ 50° C. | |
| | Hydrate Cycle: | 2 hours @ 45° C. in water | |
| C. | Results | Wall thickness: (0.015″) | |
| | | Internal diameter: (4 mm) | |
| | | Color: good | |
| | | Transparency: good | |
| | | Surface: smooth | |

No. 10

The procedure of Example 1 was repeated under the following conditions:

| A. | VIVATHANE ™ | 3.0 ml | Pre-starting |
| --- | --- | --- | --- |
| | Diisobutyladipate | 2.5 ml | prosthesis material |
| | MEK | 1.25 ml | |
| B. | Spindle Cure: | 1.5 hours @ 24° C. @ 25 rpms | |
| | Oven Cure: | 4.0 hours @ 50° C. | |
| | Hydrate Cycle: | 2 hours @ 45° C. in water | |
| C. | Results: | Wall thickness: 0.012″ | |
| | | Internal diameter: 4 mm | |
| | | Color: good | |
| | | Transparency: good | |
| | | Surface: smooth | |

No. 11

The procedure of Example 1 was repeated under the following conditions:

| A. | VIVATHANE ™ | 3.5 ml |
| --- | --- | --- |
| | Diisobutyladipate | 2.8 ml |
| | MEK | 1.0 ml |
| B. | Spindle Cure: | 1 hour @ 24° C. @ 20 rpms |
| | Oven Cure: | 2 hours @ 50° C. |
| | Hydrate Cycle: | 4 hours @ 45° C. in water |
| C. | Results: | Wall thickness: 0.004″ (2 wipes) |
| | | Internal diameter: 3 mm |
| | | Color: good |
| | | Transparency: good |
| | | Surface: smooth |

The formed prosthesis may vary in dimensions as desired. The inside diameter will depend upon the size of the mandrel. A typical range for micro-vascular grafts may be as fine as a diameter of 0.01 inch to 0.04 inches, with a practical upper limit (for large bore grafts) of from 1 inch or more. The larger sized film-sheet prosthesis can be cut into flat sheets or otherwise shaped for making gauze types of products, shunts, bladders, uretas, urethras, sewing rings and patches and diaphrams for various types of reconstructive surgical procedures. Preferably, the prosthesis of the invention may be from 1 mm to 6 mm in diameter. It can be widely used in the 6 mm and less diameter range.

Compliance of the inventive prosthesis varies with its use such as artery or vein and the diameter of the living vessel counterpart. Therefore, the preferable compliance for the inventive prosthesis cannot be predicted since by its very nature, compliance varies with the bore diameter and wall thickness, the bodily region to which the artificial prosthesis is applied or attached. Nevertheless, the inventive prosthesis will have a compliance closely matching that of its living vessel counterpart. Since the living vessel where the usual vascular constructive surgery is performed has a compliance value from about 0.1 to about 0.8, it is preferable that the inventive prosthesis have a compliance value from 0.1 to about 0.8. The inventive prosthesis having a compliance of from 0.1 to 0.8 can be used as arteries having a proper diameter. With an inside diameter of 6 mm or less and a compliance of from 0.1 to 0.5, it can be preferably used as arteries of small diameter.

For chain extension, in addition to the preferred MDI, modified forms of monomeric MDI or MDI-containing resins, any suitable organic diisocyanate may be used in the process of this invention such as, for example, aliphatic diisocyanates, aromatic diisocyanates, alicyclic diisocyanates, and heterocyclic diisocyanates including such as, for example, ethylene diisocyanate, ethylidene diisocyanate, propylene diisocyanate, butylene diisocyanate, cyclopentylene - 1,3 - dissocyanate, cyclohexylene - 1,4 - diisocyanate, cyclohexylene - 1,2 - diisocyanate, 2,4 - tolylene diisocyanate, 2,6-tolylene diisocyanate, 4,4' - diphenylmethane diisocyanate, 2,2 - diphenylpropane - 4,4' - diisocyanate, p-phenylene diisocyanate, m-phenylene diisocyanate, xylylene diisocyanate, 1,4 - napthylene diisocyanate, 1,5 - naphthylene diisocyanate, diphenyl - 4,4 'diisocyanate, azobenzene - 4,4' - diisocyanate, diphenylsulfone - 4,4' - diisocyanate, dichlorohexamethylene diisocyanate, tetramethylene diisocyanate, pentamethylene diisocyanate, hexamethylene diisocyanate, 1-chloroboenzene - 2,4 - diisocyanate, furfurylidene diisocyanate, triphenyl methane triisocyanate and the like.

Although the invention has been described in considerable detail for the purpose of illustration, it is to be understood that variations may be made therein by those skilled in the art without departing from the spirit of the invention and the scope of the claims.

I claim:

1. Method of fabricating prosthesis material for use with a living body which comprises:
   (a) preparing a polymerizable thermosetting material by mixing components thereof at about ambient temperature and about atmospheric pressure;
   (b) introducing the thermosetting material to the surface of tubular forming means having notability about a substantially horizontal axis thereby forming a relatively thin film of thermosetting material thereon;
   (c) subjecting the thin film to sub-atmospheric pressure at about ambient temperature thereby imparting isotropic characteristics to the film;
   (d) contacting the thin film with wiper means in order to remove excess material from the film thereby achieving desired film thickness; and
   (e) curing the thin film to a stable physical structure of prosthesis material.

2. Method according to claim 1 wherein the polymerizable thermosetting material is an oligomeric diaminobenzoate.

3. Method according to claim 2 wherein the oligomeric diaminobenzoate is chain extended by a modified diphenylmethane diisocyanate.

4. Method according to claim 3 wherein the elasticity of the material is selected by the addition of a polymer linkage modifier of the diisobutyl adipate class.

5. Method according to claim 3 wherein the ratio of oligomeric diaminobenzoate to modified diphenylmethane diisocyanate is from 1:3 to 6:7 by volume.

6. Method according to claim 5 wherein the surface of the prosthesis material is optically flat and the material has a compliance value ranging from 0.1 to 0.8.

7. Method according to claim 6 wherein the film thickness is from 0.001 to 0.03 inches.

8. A blood and tissue compatible artificial prosthesis material prepared in accordance with claims 1, 2, 3, 4, 5, 6 or 7 wherein the prosthesis has physical properties of compliance approximating those of organic tissue counterpart.

9. Artificial prosthesis material according to claim 8 wherein the material is configured as a nerve cuff.

10. Artificial prosthesis material according to claim 8 wherein the material is formed in a sheet structure suitable for protective or prosthesis application for skin.

11. Artificial prosthesis duct formed in accordance with claim 8.

12. Artificial prosthesis vascular graft formed in accordance with claim 8.

13. Method for replacing soft body tissue comprising:
    (a) preparing prosthesis material in accordance with the method of claims 1, 2, 3, 4, 5, 6, or 7; and
    (b) applying the prosthesis material to a portion of a living body to form an integral combination of prosthesis material and living tissue.

14. Method of fabricating an artificial prosthesis material for use with a living body which comprises:
    (a) preparing a liquid polymer solution having thermosetting properties and physical properties of compliance and elasticity substantially the same as that of soft body tissue by mixing desired components at about atmospheric pressure and about ambient temperature;
    (b) depositing an excess of the polymer solution to the surface of a substantially horizontal rotating mandrel located in housing means;
    (c) subjecting at least a portion of the interior of the housing means to sub-atmospheric pressure sufficient to degas the deposited polymer solution;
    (d) contacting the deposited polymer solution on the rotating mandrel with wiper means thereby adjusting the thickness of the polymer solution on the rotating mandrel to desired thickness;
    (e) curing the polymer solution on the rotating mandrel in the housing means for a first predetermined time and at about ambient temperature and about atmospheric pressure sufficient to initially cure the polymer to a tacky state;
    (f) removing the mandrel having deposited thereon the initially cured polymer from the housing means;
    (g) subjecting the initially cured polymer to temperature and pressure conditions and at second predetermined time sufficient to finally cure the polymer to a stable physical structure of prosthesis material;
    (h) immersing the mandrel having deposited thereon the stable physical structure of prosthesis material in an aqueous solution under conditions sufficient to cause a thin film of aqueous solution to be deposited between the outer surface of the mandrel and the inner surface of the cured polymer; and
    (i) removing the prosthesis material from the mandrel.

15. Method according to claim 14 wherein the first predetermined time is less than the second predetermined time and the conditions sufficient to deposit a thin film of aqueous solution include a temperature less than the temperature sufficient to finally cure the polymer.

16. Method according to claim 15 wherein the polymer solution comprises oligomeric diaminobenzoate extended with methylene bis-p-phenyl-isocyanate or with methylene diisocyanate.

17. A blood and tissue compatible artificial prosthesis material fabricated in accordance with claims 14, 15 or 16.

18. Artificial prosthesis material according to claim 17 wherein the material is configured as a nerve cuff.

19. Artificial prosthesis material according to claim 17 wherein the material is formed in a sheet structure suitable for protective or prosthesis application for skin.

20. Artificial prosthesis duct formed in accordance with claim 17.

21. Artificial prosthesis vascular graft formed in accordance with claim 17.

22. Vascular graft in accordance with claim 21 wherein the graft has an inner diameter of 6 mm or less.

23. Method for replacing soft body tissue comprising:
    (a) fabricating prosthesis material in accordance with the method of claims 14, 15, or 16; and
    (b) applying the prosthesis material to a portion of a living body to form an integral combination of prosthesis material and living tissue.

* * * * *